United States Patent
Zhang et al.

(10) Patent No.: US 9,060,974 B1
(45) Date of Patent: Jun. 23, 2015

(54) PROSTATE CANCER THERAPY USING AN ENGINEERED RESPIRATORY SYNCYTIAL VIRUS

(76) Inventors: Weidong Zhang, Tampa, FL (US);
Lixian Jiang, Wesley Chapel, FL (US);
Calvin Cao, Tampa, FL (US)

( * ) Notice: Subject to any disclaimer, the term of this patent is extended or adjusted under 35 U.S.C. 154(b) by 561 days.

(21) Appl. No.: 13/134,326

(22) Filed: Jun. 6, 2011

(51) Int. Cl.
*A01N 63/00* (2006.01)
*A61K 39/155* (2006.01)

(52) U.S. Cl.
CPC ...... *A61K 39/155* (2013.01); *C12N 2760/18032* (2013.01); *C12N 2760/18532* (2013.01)

(58) Field of Classification Search
CPC .................. A61K 39/155; C12N 2760/18032; C12N 2760/18532
USPC .............................................. 424/93.6, 211.1
See application file for complete search history.

(56) References Cited

U.S. PATENT DOCUMENTS

| 6,986,881 B1 | 1/2006 | Livingston et al. |
| 7,709,007 B2 | 5/2010 | Murphy et al. |
| 2004/0109877 A1 | 6/2004 | Palese et al. |
| 2010/0303839 A1 | 12/2010 | Bose et al. |

OTHER PUBLICATIONS

Everts et al., 2005, Cancer Gene Therapy, vol. 12, p. 141-161.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002,, Virology, vol. 304, p. 135-145.*
Chattopadhyay et al., 2004, Virus Research, vol. 99, p. 139-145.*
Muster et al. (2004) Int. J. Cancer 110, 15-21.
Restifo et al. (1998) Virology 249, 89-97.
Shayakhmetov et al. (2004) J. Virology 78, 5368-81.
Spann et al. (2004) J. Virology 78, 4363-69.
Munir et al. (2008) J. Virology 82, 8780-96.
Hao et al. (2007) Molecular Cancer Therapeutics 6, 2220-29.
Mohapatra et al. (2007) Molecular Cancer Research 5, 141-151.
Everts et al. (2005) Cancer Gene Therapy, 12, 141-161.
Chattopadhyay et al. (2004) Virus Research, 99, 139-145.
Smallwood et al. (2002) Virology, 304, 135-145.
Tomasinsig et al. (2005) Current Protein and Peptide Science, 6, 23-34.
Skolnick et al. (2000) Trends in Biotech, 18, 34-39.

* cited by examiner

*Primary Examiner* — Shin Lin Chen

(57) ABSTRACT

The present invention is within the field of oncolytic virotherapy. Oncolytic virotherapy is a strategy using viruses, naturally occurring or genetically modified, to selectively target and destroy tumor cells while leaving surrounding non-malignant cells unharmed Here, an engineered respiratory syncytial virus (RSV), with the NS1 gene deleted (NS1 gene-deficient RSV, ΔNS1 RSV), kills prostate cancer cells, but does not affect normal human cells.

3 Claims, 4 Drawing Sheets

PROSTATE CANCER THERAPY USING AN ENGINEERED RESPIRATORY SYNCYTIAL VIRUS

CROSS-REFERENCE TO RELATED APPLICATIONS

This application claims priority to U.S. non-provisional application Ser. No. 12/800,585 filed on May 18, 2010, issued as U.S. Pat. No. 8,597,637, U.S. provisional Application No. 61/398,236 filed on Jun. 22, 2010, and non-provisional application Ser. No. 12/925,886 filed on Nov. 2, 2010, now abandoned, the disclosures of which are incorporated herein in their entirety.

DESCRIPTION

Field of the Invention

The invention is within the scope of oncolytic virotherapy. We engineered respiratory syncytial virus (RSV) by deleting NS1 gene, and found that the NS1 gene deficient RSV (ΔNS1 RSV) can kill prostate cancer cells, but not normal human cells.

BACKGROUND OF THE INVENTION

Prostate cancer is the most common malignancy and the second leading cause of cancer mortality amongst men in the Western world. In the USA, there is an estimated incidence of 217,730 cases and 32,050 deaths in 2010. Up to 40% of men diagnosed with prostate cancer will eventually develop metastatic disease, and although most respond to initial medical or surgical castration, progression to castration resistance is universal. The average survival for patients with castration-resistant prostate cancer is 2-3 year[1]. It continues to be a major cause of cancer-related morbidity and mortality, and there is an urgent need for new treatments.

Oncolytic Virotherapy.

Oncolytic virotherapy is a novel strategy using viruses, either naturally occurring or genetically modified, to selectively target and destroy tumor cells while leaving surrounding non-malignant cells unharmed [2]. Our preliminary data show that ΔNS1 RSV, not wt RSV, specifically kills prostate cancer cells (LN Cap cells) (FIG. 2), and ΔNS1 RSVNS1 protein functions as an anti-apoptotic factor and deletion of NS1 restores the apoptotic pathway in tumor cells.

Biology of RSV NS1 Protein.

RSV genome contains individual genes for ten viral proteins [3]. The transcription of RSV genes is polar, with the promoter-proximal genes being transcribed more frequently than the promoter-distal ones. The NS1 gene is promoter-proximally located at the 3' end of the viral genome and therefore its mRNA is the most abundant of the RSV transcripts in a linear start-stop-restart mode[4] (FIG. 1). NS1 protein is referred to as nonstructural since it has not been detected in RSV particles. NS1 is exclusively found in RSV-infected cells. Our group, along with others, has found that NS1 can counter the type I IFN signaling during RSV infection[5, 6], implying that NS1 plays a direct role in inhibiting the host's innate immune response.

ΔNS1 RSV Induces Apoptosis in Human Prostate Cancer Cells.

Evasion from apoptotic cell death unregulated cell proliferation and eventual tumor development is one of the hallmarks of oncogenic cell transformation. We found that ΔNS1 RSV selectively induces apoptosis in tumor cells as we demonstrated in our previous patent application Ser. No. 12/925,886, and also generated CPE in prostate cancer cells (FIG. 2), suggesting that multiply mechanism-mediated cell death participates in the anti-tumor effect of ΔNS1 RSV.

RSV can be rendered nonpathogenic by mutating the NS1 gene so that it no longer inhibits IFN release, which attenuates viral infection in normal cells. However, these nonpathogenic RSV, ΔNS1 RSV, are still oncolytic because tumor cells are defective in their ability to produce and respond to IFN and, therefore, efficiently support the propagation of ΔNS1 RSV and ΔNS1 RSV kills tumor cells.

SUMMARY

This invention discloses a NS1 gene deficient RSV (ΔNS1 RSV), which could be utilize to kill prostate cancer cells, but not normal human cells. In one embodiment, the gene NS1 is deleted by the removal of 122 to 630 nt in the antigenomic cDNA using reverse genetics approach, resulting in the joining of the upstream nontranslated region of NS1 to the translational initiation codon of NS2. The ΔNS1 RSV was recovered through co-transfecting Vero cells with the NS1-deficient RSV cDNA and expressional plasmids encoding N, P, M2-1 and L. The RSV NS1 protein functions as a type-I-IFN antagonist, ΔNS1 RSV virotherapy produces more type-I-IFN, which prevents virus from replication in normal cells and also induces antitumor effects.

In another embodiment, the engineered virus could be any other virus having a similar strategy to delete NS1 gene, which functions as a gene encoding the related protein as a type-I-IFN antagonist.

In another embodiment, the ΔNS1 RSV can be applied to cancer spot by direct injection. Or the ΔNS1 RSV can be delivered to cancer spot through blood transfusion.

Figure 1:
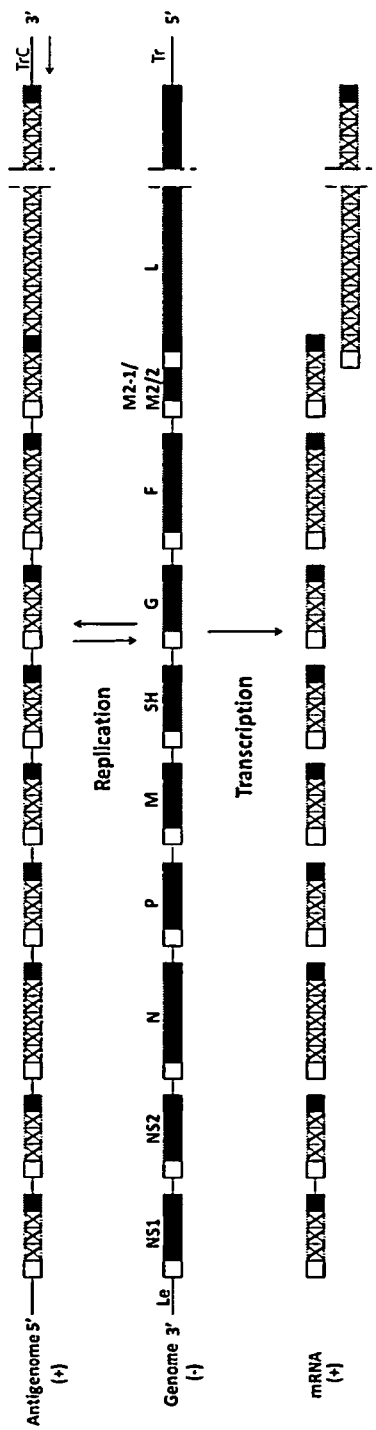
FIG. 1. Diagram of the RSV genome and its transcription and replication products. The virus genes are depicted as grey rectangles; the L gene, which comprises almost half of the genome, has been truncated. The GS and GE signals are shown as white and black boxes, respectively. The encoded anti-genome and mRNAs are indicated by hatched rectangles. Arrows indicate the location of the promoters.
Figure 2:
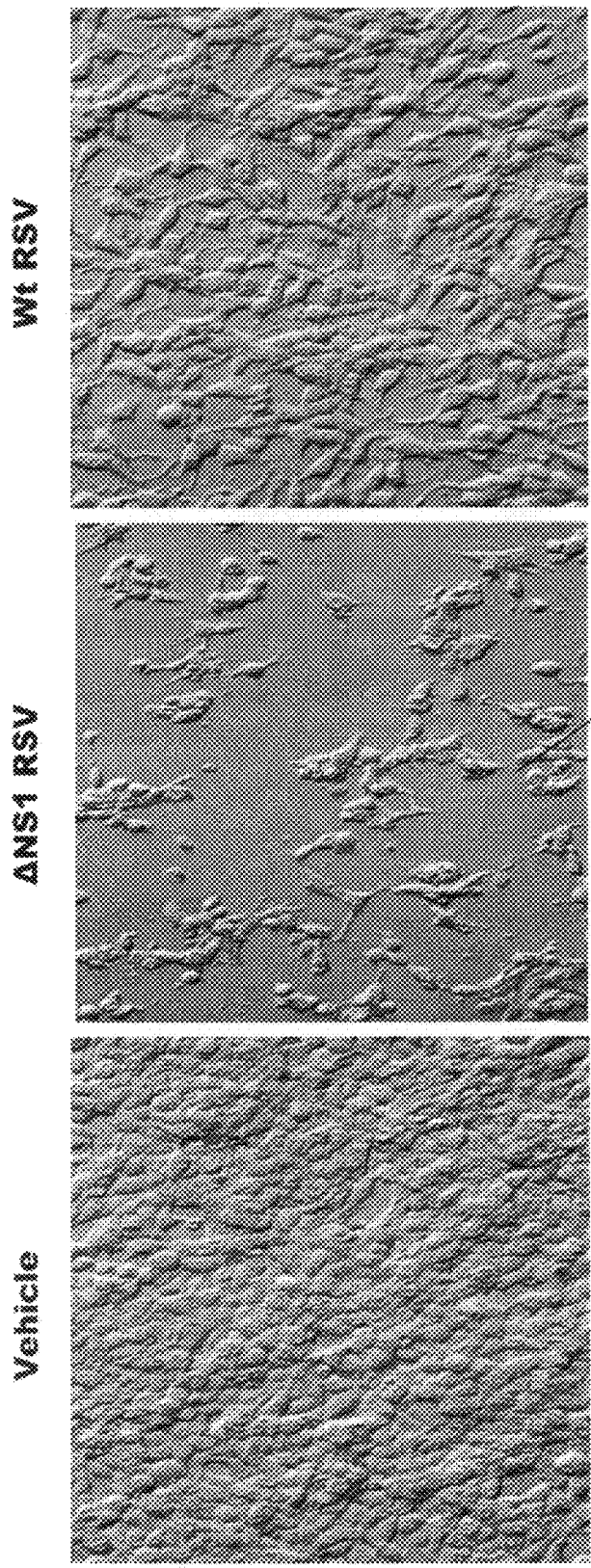
FIG. 2. Virus infection of prostate cancer cells. Morphology of virus-infected LN Cap cells 24 h post-infection. ΔNS1 RSV, not wt RSV, induced cytopathic effect (CPE) in human prostate cancer cells.
Figure 3:
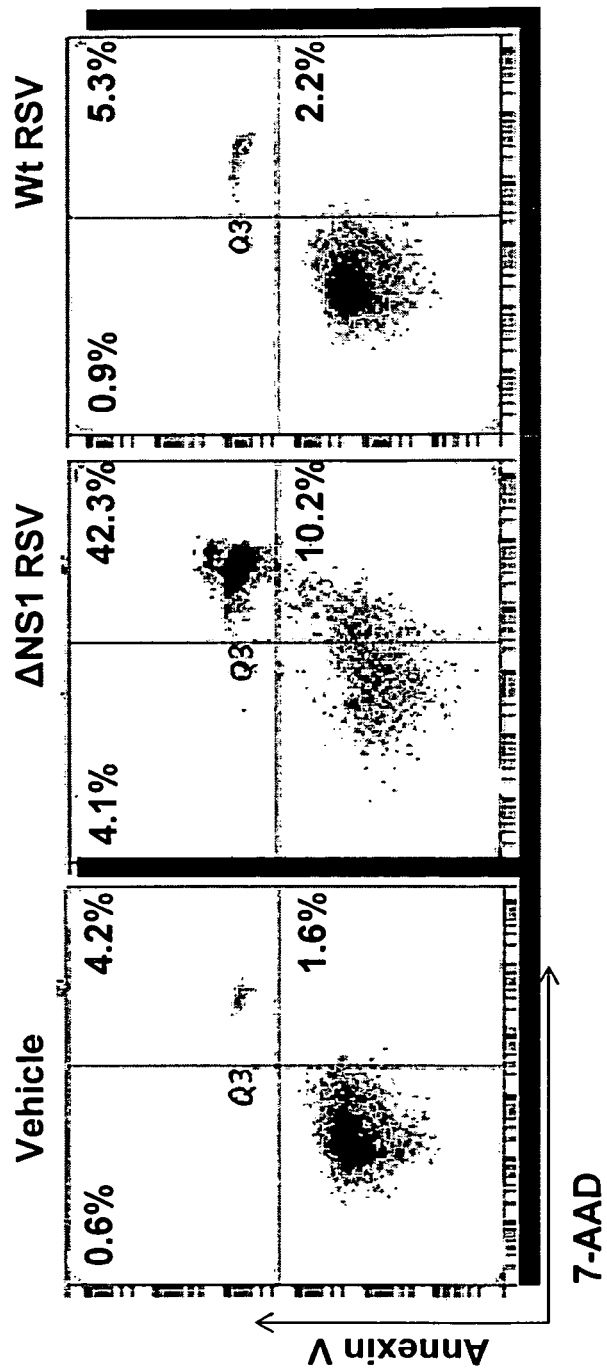
FIG. 3. ΔNS1 RSV infection induces apoptosis in prostate cancer cells. LN Cap cells were infected with indicated viruses (MOI=5), and collected 24 h post-infection, respectively, cell apoptosis was analyzed using annexin V-binding and PI uptake assay.
Figure 4:
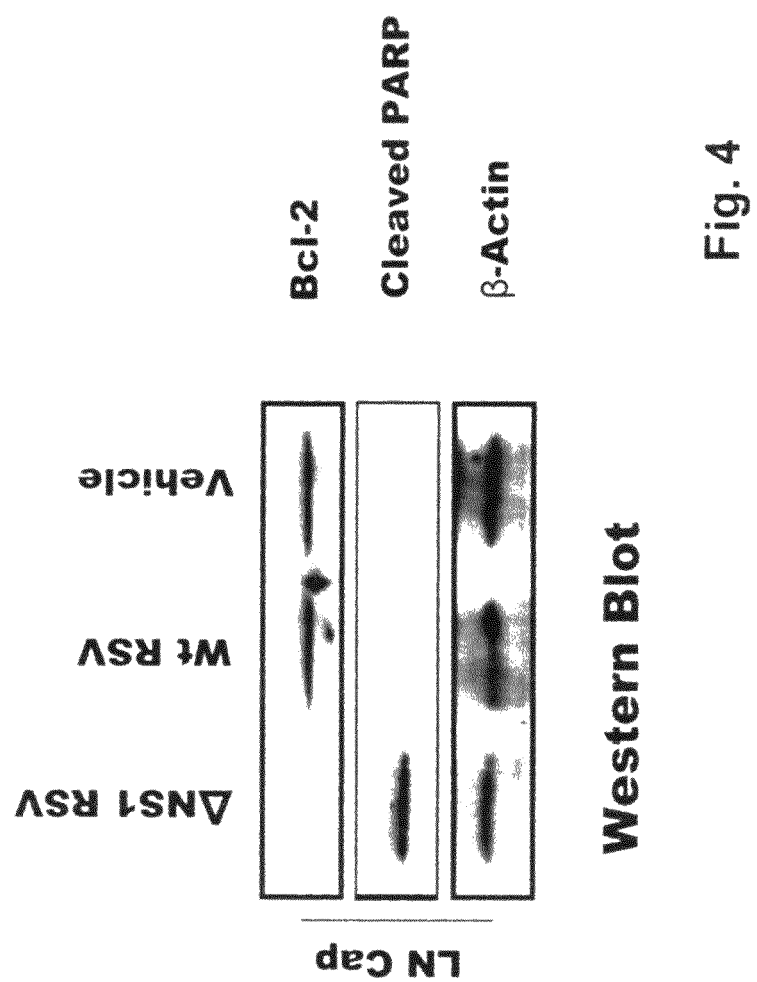
FIG. 4. Verify virus-induced apoptosis in prostate cancer cells by immunoblotting using indicated antibodies. LN Cap cell-pellets were collected 24 h post-infection, and whole cell-lysates were immunoblotted.

Table 1. Cytopathic effect (CPE) test showing ΔNS1 RSV kills human prostate cancer cells.

DETAILED DESCRIPTION OF THE INVENTION

The respiratory syncytial virus (RSV) was used in this study. The NS1 gene was deleted by the removal of 122 to 630 nt in the antigenomic cDNA using reverse genetics approach, resulting in the joining of the upstream nontranslated region of NS1 to the translational initiation codon of NS2. The ΔNS1

RSV was recovered through co-transfecting Vero cells with the NS1-deficient viral cDNA clone and expressional plasmids encoding N, P, M2-1 and L. Alternatively, the engineered virus could be any other viruses with the deletion of similar NS1 gene.

ΔNS1 RSV Preferentially Kills LN CAP Cells In Vitro.

LN CAP prostate cancer cells were infected with wt or ΔNS1 RSV (MOI=5). FIG. 2 shows that ΔNS1 RSV selectively induces CPE in LN CAP cells. Whereas, vehicle and wild type RSV has no effect on prostate cancer cells (FIG. 2). As shown in Table 1, ΔNS1 RSV, but not wt RSV, preferentially kills LN Cap prostate cancer cells and PC3 prostate cancer cells.

ΔNS1 RSV Infection Induces Apoptosis in Tumor Cells.

To test the differential effect of virus infection on apoptosis, LN CAP prostate cancer cells were infected with the indicated virusess (wt RSV) (MOI=5) and apoptosis was measured by the annexin V binding assay. FIG. 3 shows that ΔNS1 RSV selectively induces apoptosis in tumor cells, compared to the cell spontaneous apoptosis shown in controls, which was verified by immunoblotting (FIG. 4), where anti-apoptosis marker bcl-2 was not observed in ΔNS1 RSV infected cells.

REFERENCE

1. Beltran, H., et al., *New Therapies for Castration-Resistant Prostate Cancer: Efficacy and Safety*. Eur Urol.
2. Spann, K. M., et al., *Suppression of the induction of alpha, beta, and lambda interferons by the NS1 and NS2 proteins of human respiratory syncytial virus in human epithelial cells and macrophages [corrected]*. J Virol, 2004. 78(8): p. 4363-9.
3. Collins, P. L., Y. T. Huang, and G. W. Wertz, *Identification of a tenth mRNA of respiratory syncytial virus and assignment of polypeptides to the 10 viral genes*. J Virol, 1984. 49(2): p. 572-8.
4. Tran, K. C., P. L. Collins, and M. N. Teng, *Effects of altering the transcription termination signals of respiratory syncytial virus on viral gene expression and growth in vitro and in vivo*. J Virol, 2004. 78(2): p. 692-9.
5. Zhang, W., et al., *Inhibition of respiratory syncytial virus infection with intranasal siRNA nanoparticles targeting the viral NS1 gene*. Nat Med, 2005. 11(1): p. 56-62.
6. Spann, K. M., et al., *Suppression of the induction of alpha, beta, and lambda interferons by the NS1 and NS2 proteins of human respiratory syncytial virus in human epithelial cells and macrophages [corrected]*. J Virol, 2004. 78(8): p. 4363-9.

TABLE 1

ΔNS1 RSV selectively kills human prostate cancer cells

| | Virus (MOI = 5) CPE (hr post-infection) | | | |
|---|---|---|---|---|
| | 24 hr | | 48 hr | |
| Cells | ΔNS1 RSV | wt RSV | ΔNS1 RSV | wt RSV |
| PCS-440-010 (Human Primary Prostate Epithelial Cells, Normal) | — | — | — | — |
| LN Cap | ++++ | — | NO | — |
| PC3 | ++ | — | ++++ | — |

Note:
—: no CPE;
++: CPE ≤ 50%;
++++: CPE ≥ 75%;
NO: not tested;

The invention claimed is:

1. A method to treat prostate cancer in a patient in need thereof by delivering directly to the cancer an oncolytic engineered respiratory syncytial virus (RSV) with the NS1 gene deleted, wherein the RSV infects and causes oncolysis to thereby treat the patient.

2. The method of claim 1, wherein the engineered RSV is suspended in saline.

3. The method of claim 1, wherein the engineered RSV is suspended in medium.

* * * * *